(12) United States Patent
Nakada

(10) Patent No.: US 9,355,216 B2
(45) Date of Patent: *May 31, 2016

(54) USING IPTV AS HEALTH MONITOR

(71) Applicant: Sony Corporation, Tokyo (JP)

(72) Inventor: Lino Mitsuo Nakada, San Diego, CA (US)

(73) Assignee: Sony Corporation, Tokyo (JP)

( * ) Notice: Subject to any disclaimer, the term of this patent is extended or adjusted under 35 U.S.C. 154(b) by 368 days.

This patent is subject to a terminal disclaimer.

(21) Appl. No.: 14/055,483

(22) Filed: Oct. 16, 2013

(65) Prior Publication Data
US 2014/0040951 A1   Feb. 6, 2014

Related U.S. Application Data

(63) Continuation of application No. 13/644,631, filed on Oct. 4, 2012, now Pat. No. 8,648,725, which is a continuation of application No. 12/828,451, filed on Jul. 1, 2010, now Pat. No. 8,334,789.

(51) Int. Cl.
*H04N 7/173* (2011.01)
*G06F 19/00* (2011.01)
*A61B 5/024* (2006.01)
*A61B 5/00* (2006.01)
*H04L 29/08* (2006.01)
*G08B 21/04* (2006.01)
*A61B 5/02* (2006.01)
*H04N 21/475* (2011.01)
*H04N 21/478* (2011.01)
*H04N 21/488* (2011.01)
(Continued)

(52) U.S. Cl.
CPC .......... *G06F 19/3418* (2013.01); *A61B 5/0002* (2013.01); *A61B 5/0022* (2013.01); *A61B 5/0024* (2013.01); *A61B 5/02* (2013.01); *A61B 5/024* (2013.01); *A61B 5/0205* (2013.01); *A61B 5/681* (2013.01); *A61B 5/7282* (2013.01); *A61B 5/743* (2013.01); *A61B 5/7435* (2013.01); *A61B 5/7475* (2013.01); *A61B 19/44* (2013.01); *G06F 19/3406* (2013.01); *G08B 21/0453* (2013.01); *H04L 67/12* (2013.01); *H04N 21/478* (2013.01); *H04N 21/4751* (2013.01); *H04N 21/4753* (2013.01); *H04N 21/488* (2013.01); *A61B 5/021* (2013.01); *A61B 5/02055* (2013.01); *A61B 5/14532* (2013.01)

(58) Field of Classification Search
USPC ......... 725/133, 141, 153; 340/573.1, 870, 16; 345/156; 600/301
See application file for complete search history.

(56) References Cited

U.S. PATENT DOCUMENTS

| | | |
|---|---|---|
| 4,803,625 A | 2/1989 | Fu et al. |
| 5,598,849 A | 2/1997 | Browne |

(Continued)

OTHER PUBLICATIONS

Lino Mistuo Nakada, "Using IPTV as Health Monitor", file History of related U.S. Appl. No. 14/055,483, filed Jun. 12, 2015.

(Continued)

*Primary Examiner* — Hunter B Lonsberry
(74) *Attorney, Agent, or Firm* — John L. Rogitz

(57) ABSTRACT

An IPTV can receive a user name and present a screen enabling a user by means of a remote control to select health information categories, inputting numeric parameters into the selected categories which can be uploaded to an Internet server for analysis and viewed by the user for subsequent monitoring/charting.

15 Claims, 1 Drawing Sheet

(51) Int. Cl.
*A61B 19/00* (2006.01)
*A61B 5/0205* (2006.01)
*A61B 5/021* (2006.01)
*A61B 5/145* (2006.01)

(56) References Cited

U.S. PATENT DOCUMENTS

| | | | |
|---|---|---|---|
| 5,601,435 | A | 2/1997 | Quy |
| 5,776,056 | A | 7/1998 | Bu et al. |
| 6,800,059 | B2 | 10/2004 | Muraki et al. |
| 6,936,007 | B2 | 8/2005 | Quy |
| 8,334,789 | B2 * | 12/2012 | Nakada ................ A61B 5/0002 340/573.1 |
| 8,501,093 | B2 | 8/2013 | Rutkowski et al. |
| 8,648,725 | B2 * | 2/2014 | Nakada ................ A61B 5/0002 340/573.1 |
| 8,684,900 | B2 | 4/2014 | Tran |
| 9,075,905 | B2 * | 7/2015 | Nakada ................ A61B 5/0002 |
| 2003/0208110 | A1 | 11/2003 | Mault et al. |
| 2007/0073173 | A1 | 3/2007 | Lam et al. |
| 2007/0204297 | A1 | 8/2007 | Gonzalez |
| 2008/0154099 | A1 | 6/2008 | Aspel et al. |
| 2009/0012373 | A1 | 1/2009 | Raij et al. |
| 2010/0225501 | A1 | 9/2010 | Grubis et al. |
| 2013/0095459 | A1 | 4/2013 | Tran |

OTHER PUBLICATIONS

Lino Mitsuo Nakada, "Using IPTV as Health Monitor", related pending U.S. Appl. No. 14/737,860 non-final office action dated Dec. 31, 2015.

Lino Mitsuo Nakada, "Using IPTV as Health Monitor", related pending U.S. Appl. No. 14/737,860 applicants response to non-final office action filed Jan. 8, 2016.

* cited by examiner

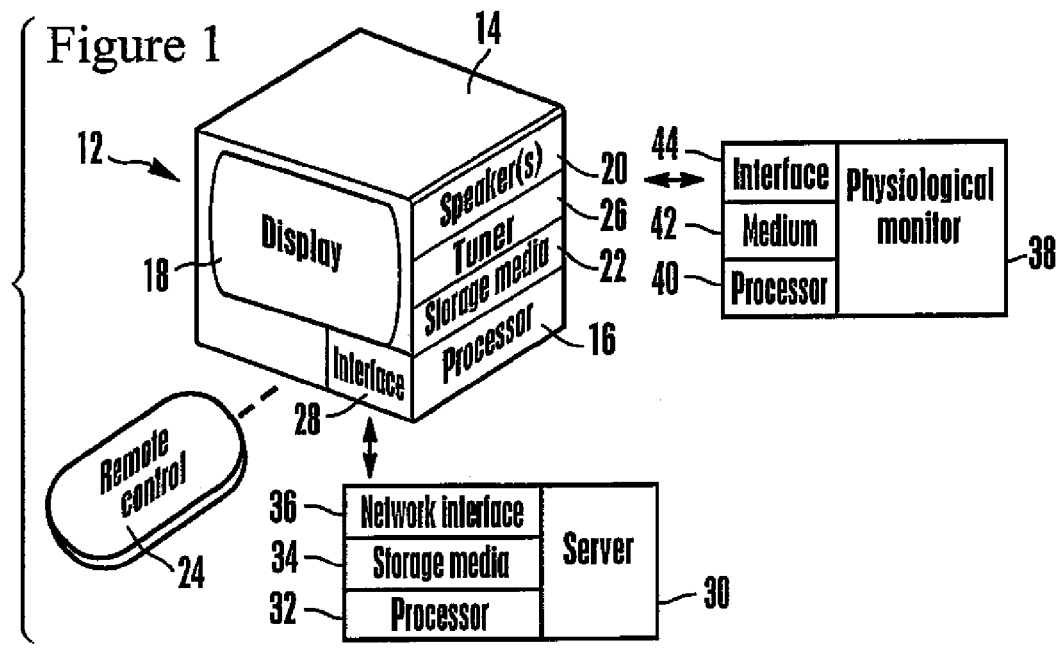
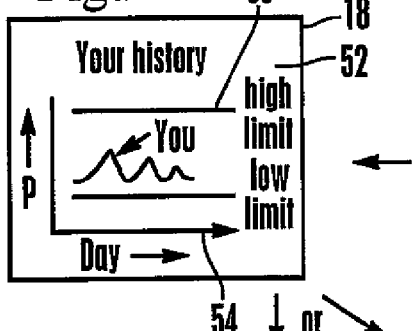

USING IPTV AS HEALTH MONITOR

I. FIELD OF THE INVENTION

The present application relates generally to using Internet Protocol TVs (IPTVs) as health monitors.

II. BACKGROUND OF THE INVENTION

Internet access through TVs is typically provided by essentially programming the TV (often referred to as an Internet Protocol TV, or IPTV) as though it were a computer executing a browser. As understood herein, such devices can be leveraged for many novel uses owing to their connectivity to the Internet.

As also understood herein, with an aging populace it is important to provide people, particularly the elderly, with an easy, intuitive means to track their health. In this way, they can better adjust their habits, meals, etc. to achieve a healthy lifestyle. Present principles seek to leverage TV technology, which is readily understood and frequently used by people, to assist in enabling people to monitor their health.

SUMMARY OF THE INVENTION

Accordingly, an IPTV has a housing, a display on the housing, a network interface, a TV tuner, and a processor in the housing controlling the display and TV tuner and communicating with the Internet through the network interface. An input device communicates with the processor. The processor executes logic that includes presenting a first user interface (UI) on the display enabling a person to log in to a health monitoring feature with a user name and password and/or to create a new account, such that the IPTV maintains health records by user name, so that it may monitor plural people. The processor also presents a second UI on the display listing multiple parameters from which a person may select one or more to monitor by means of the input device. Further, the processor presents a third UI on the display responsive to a person selecting a parameter from the second UI allowing a person to enter by means of the input device numbers associated with a measurement of the parameter, and also records a time of receipt of the numbers. A fourth UI is presented on the display presenting a history of measurements of the parameter associated with the person.

In some embodiments the parameters on the second UI include "blood pressure" and "blood glucose". Numbers representing a parameter may be received automatically from a parameter monitor.

In examples, the fourth UI includes a graph of time on an x-axis versus parameter value on a y-axis. The fourth UI can also present upper and/or lower limit lines established per standard of care guidance as to what upper and/or lower "safe" limits of the parameter being displayed are.

Additionally, in example implementations the processor presents a fifth UI on the display when the numbers associated with a measurement of the parameter are within guidelines, advising the user of such. The fifth UI can be presented automatically on the display after a predetermined period of time during which the fourth UI appears on the display. Similarly, the processor may present a sixth UI on the display when the numbers associated with a measurement of the parameter are not within guidelines, advising the user of such. In this latter case the processor can automatically contact a medical caregiver responsive to the numbers associated with a measurement of the parameter not being within guidelines, with the user being afforded the choice of disabling and enabling the automatic call feature.

In another aspect, a method includes receiving, at a TV, user input indicating an identity of a user. The method also includes receiving, at the TV, numeric input representing a measurable physical parameter of the user, and storing a time associated with the numeric input along with the input. A visualization of the user's history of the measurable physical parameter is presented on the TV.

In another aspect, an apparatus includes a video display, a network interface, a TV tuner, and a processor controlling the display and TV tuner and communicating with the Internet through the network interface. An input device communicates with the processor, which executes logic that includes receiving user input indicating an identity of a user and receiving numeric input representing a measurable physical parameter of the user. The logic also includes storing a time associated with the numeric input along with the input. A visualization of the user's history of the measurable physical parameter is presented on the display.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a block diagram of an example system in accordance with present principles; and FIGS. 2-7 are example screen shots that can be presented on the IPTV in accordance with present principles for enabling a person to monitor his health.

DETAILED DESCRIPTION OF THE PREFERRED EMBODIMENT

Referring initially to FIG. 1, an IPTV 12 includes a housing 14 bearing a digital processor 16. The processor 16 can control a visual display 18 and an audible display 20 such as one or more speakers. To undertake present principles, the processor 16 may access one or more computer readable storage media 22 such as but not limited to RAM-based storage (e.g., a chip implementing dynamic random access memory (DRAM)) or flash memory or disk-based-storage. Software code implementing present logic executable by the IPTV 12 may also be stored on one of the memories shown to undertake present principles.

The processor 16 can receive user input signals from various input devices including a remote control device 24, a point and click device such as a mouse, a keypad, etc. A TV tuner 26 may be provided to receive TV signals from a source such as a set-top box, satellite receiver, cable head end, terrestrial TV signal antenna, etc. Signals from the tuner 26 are sent to the processor 16 for presentation on the display 18 and speakers 20.

As shown in FIG. 1, a network interface 28 such as a wired or wireless modem or wireless telephony transceiver communicates with the processor 16 to provide connectivity to a wide area network such as the Internet. Double arrows in FIG. 1 indicate network communication between components over wired and/or wireless links. In this way, the IPTV 12 can communicate with a management server 30 on the Internet with processor 32 accessing one or more non-transitory computer readable storage media 34 and communicating with a wide area network such as the Internet via a network interface 36.

In some implementations one or more physiological monitors 38 such as a blood pressure monitor, a blood glucose monitor, a heart rate monitor, a weight gauge a thermometer, etc. may be provided that can be engaged with a patient to measure a physical parameter and then automatically transmit the result of the measurement to the IPTV. The monitor 38 shown in FIG. 1 includes a monitor processor 40 accessing a computer readable storage medium 42 and communicating with the IPTV 12 using a wired or wireless communication interface 44 such as a network interface, a Bluetooth interface, a universal serial bus (USB) interface, etc.

FIGS. 2-7 illustrate example principles. FIG. 2 shows that a user interface (UI) 46 may be presented on the display 18 to enable a person to log in to the health monitoring feature with a user name and password or to create a new account. Thus, it will be appreciated that the IPTV 12 maintains health records by user name, so that it may monitor multiple people confidentially.

Assuming successful log in, a UI 48 may be presented on the display 18 as shown in FIG. 3, listing multiple parameters from which a person may select one or more to monitor. For example, "blood pressure" may be selected to cause a UI 50 shown in FIG. 4 to appear, containing fields into which the user may enter his systolic and diastolic numbers as measured by the physiological monitor 38 using the keys on the RC 24. Or, upon selection of "blood pressure" the IPTV 12 may automatically contact nearby blood pressure monitors such as the physiological monitor 38 when implemented as such and request that the monitor 38 transmit to the IPTV 12 the most recent measurement. Regardless of how received, the date and time of receipt of the measurement preferably is recorded. Subsequent to inputting "blood pressure" the user may return to the UI 48 shown in FIG. 3 to select "glucose" to input the person's recently measured glucose or "heart rate" to input the user's recently measured heart rate, etc. In example implementations the UI 48 may include additional parameters that may be defined or edited by users.

The user may elect to invoke the UI 52 of FIG. 5 to view the history of the parameter input in FIG. 4. As shown, in one embodiment the UI 52 presents a graph 54 of time (on the x-axis) versus parameter value (on the y-axis) so that the user may see how the parameter is varying over time. Also, upper and/or lower limit lines 56 may be provided which are established per standard of care guidance as to what the upper and/or lower "safe" limits of the parameter being displayed are. In this way, the user can compare his measured parameter against medically established guidelines.

When the user is within the guidelines, the UI 58 of FIG. 6 may be presented on the display 18 after, e.g., a predetermined period of time during which the UI 52 of FIG. 5 appears. The UI 58 informs the user that his measurements for the parameter are within normal guidelines. In contrast, if a measurement falls outside the guidelines, the UI 60 of FIG. 7 may appear, advising the user to contact his medical caregiver. Also, in the account set up the user may elect to input caregiver contact information such as telephone number or network address or email, and if desired when the UI 60 of FIG. 7 is presented the processor 16 may also automatically transmit the out-of-specification measurement to the caregiver's address or telephone number (by, e.g., text entry). The automatic alert feature described above may be enabled and disabled as desired by the user using a monitor setup UI listing the automatic contact feature with selector elements for enabling and disabling it.

While the particular USING IPTV AS HEALTH MONITOR is herein shown and described in detail, it is to be understood that the subject matter which is encompassed by the present invention is limited only by the claims.

What is claimed is:

1. Method, comprising:
receiving from a user interface, input indicating an identity of a person;
receiving from direct user input and/or from a biological sensor with the person, input representing a physical parameter of the person;
storing a time associated with the numeric input along with the input representing the physical parameter;
outputting for display a visualization the person's history of the measurable physical parameter; and
outputting for display at least one selectable parameter selectable to input numbers representative thereof, the at least one selectable parameter including "blood pressure" and/or "blood glucose", wherein the visualization includes upper and/or lower limit lines representing upper and/or lower "safe" limits of the parameter being displayed.

2. The method of claim 1, comprising presenting a message automatically on the display after a predetermined period of time during which the visualization appears on the display advising that the numeric input is not within guidelines.

3. The method of claim 2, comprising automatically contacting a medical caregiver responsive to the numeric input not being within guidelines.

4. The method of claim 3, comprising enabling a user to disable and enable automatically contacting a medical caregiver.

5. Apparatus comprising:
processor configured for controlling a display and for communicating with the Internet through a network interface;
the processor configured for accessing instructions on a computer readable storage medium for configuring the processor for executing logic including:
receiving first input indicating an identity of a user;
receiving second input representing a physical parameter of the user;
storing a time associated with the second input;
presenting on the display a visualization of the user's history of the measurable physical parameter; and
outputting for presentation on the display at least one selectable parameter selectable to input numbers representative thereof, the at least one selectable parameter including "blood pressure" and/or "blood glucose", wherein the visualization includes a graph of time versus parameter value and upper and/or lower limit lines indicating upper and/or lower "safe" limits of the parameter being displayed.

6. The apparatus of claim 5, wherein the logic executed by the processor includes presenting on the display the at least one selectable parameters.

7. The apparatus of claim 5, wherein the visualization includes a graph of time on an x-axis versus parameter value on a y-axis.

8. Apparatus comprising:
processor configured for controlling a display and for communicating with the Internet through a network interface;
the processor configured for accessing instructions on a computer readable storage medium for executing the instructions for configuring the processor for:
presenting a first user interface (UI) on the display enabling a person to log in to a health monitoring feature, such that the apparatus maintains health records by user name, so that it may monitor plural people;

presenting a second UI on the display listing multiple parameters from which a person may select one or more to monitor by means of the input device;

presenting a third UI on the display allowing a person to enter by means of the input device numbers associated with a measurement of the parameter;

recording at least a time of receipt of the numbers;

presenting a fourth UI on the display presenting a history of measurements of the parameter associated with the person;

wherein the fourth UI presents upper and/or lower limit lines established per standard of care guidance as to what upper and/or lower "safe" limits of the parameter being displayed are.

9. The apparatus of claim 8, wherein the parameters on the second UI include "blood pressure" and "blood glucose".

10. The apparatus of claim 8, wherein numbers representing a parameter are received automatically from a parameter monitor.

11. The apparatus of claim 8, wherein the fourth UI includes a graph of time on an x-axis versus parameter value on a y-axis.

12. The apparatus of claim 8, wherein the processor when executing the instructions s configured to present a fifth UI on the display responsive to the numbers associated with a measurement of the parameter being within guidelines, the fifth UI being presented automatically on the display after a predetermined period of time during which the fourth UI appears on the display.

13. The apparatus of claim 12, wherein the processor when executing the instructions presents a sixth UI on the display when the numbers associated with a measurement of the parameter are not within guidelines, advising the user of such.

14. The apparatus of claim 13, wherein the processor when executing the instructions automatically contacts a medical caregiver responsive to the numbers associated with a measurement of the parameter not being within guidelines.

15. The apparatus of claim 14, wherein a user can disable and enable the processor automatically contacting a medical caregiver responsive to the numbers associated with a measurement of the parameter not being within guidelines.

* * * * *